US010342191B2

(12) United States Patent
Scanlon et al.

(10) Patent No.: US 10,342,191 B2
(45) Date of Patent: Jul. 9, 2019

(54) METHOD AND APPARATUS FOR REGENERATION, ACCLIMATIZATION, AND CONDITIONING OF PLANT PROPAGULES

(71) Applicant: CannTx Life Sciences, Inc., Waterloo (CA)

(72) Inventors: Jeffrey Scanlon, Guelph (CA); Patrick Scanlon, Guelph (CA); Peter Young, Guelph (CA)

(73) Assignee: SAED TECHNOLOGIES LTD, Toronto (CA)

( * ) Notice: Subject to any disclaimer, the term of this patent is extended or adjusted under 35 U.S.C. 154(b) by 458 days.

(21) Appl. No.: 15/232,469

(22) Filed: Aug. 9, 2016

(65) Prior Publication Data

US 2018/0042193 A1 Feb. 15, 2018

(51) Int. Cl.
*A01H 4/00* (2006.01)
*A01G 9/20* (2006.01)
(Continued)

(52) U.S. Cl.
CPC .............. *A01H 4/001* (2013.01); *A01G 9/20* (2013.01); *A01G 9/247* (2013.01); *A01G 25/167* (2013.01)

(58) Field of Classification Search
CPC . A01G 9/247; A01G 9/14; A01G 9/00; A01H 4/001
See application file for complete search history.

(56) References Cited

U.S. PATENT DOCUMENTS 9,591,815 B2 * 3/2017 Fujiyama ................. A01G 9/00
10,104,843 B2 * 10/2018 Stewart .................... A01G 9/16
(Continued)

FOREIGN PATENT DOCUMENTS

CN 101300958 A 11/2008
CN 103135540 A 6/2013
(Continued)

OTHER PUBLICATIONS

Written Opinion of PCT/CA2017/050808.

*Primary Examiner* — Kristen C Hayes
(74) *Attorney, Agent, or Firm* — Cotman IP Law Group, PLC (57) ABSTRACT

A method and apparatus for the regeneration, acclimation and conditioning of in vitro derived plant propagules is presented. The apparatus comprises a regulated chamber, a laminar flow work station coupled to the regulated environment, and a supply compartment. A process control system regulates the chamber to sterile or near sterile conditions. The process control system monitors and modulates the microenvironment, nutritional profile and frequency of fertigation, atmospheric composition, as well as the quality and quantity of irradiance incident on propagules in the sterile chamber. This controlled environ optimizes propagules regeneration, and facilitates the establishment of photoautotrophism and homeostatic capacity of plant tissues. Furthermore, the apparatus allows for the metabolic and morphologic conditioning of plantlets for high intensity indoor cultivation as well as the inoculation of plantlets with beneficial bacteria and fungi which increase metabolic function and provide a protection from colonization of plantlets by pathogenic microflora through spatial occupation.

21 Claims, 8 Drawing Sheets (51) Int. Cl.
*A01G 9/24* (2006.01)
*A01G 25/16* (2006.01)

(56) References Cited

U.S. PATENT DOCUMENTS

2010/0275512 A1* 11/2010 Nien .................. A01G 9/16
                                                    47/66.7
2010/0285436 A1    11/2010 DeVore
2014/0318012 A1* 10/2014 Fujiyama ............ F24F 11/0001
                                                    47/62 R

FOREIGN PATENT DOCUMENTS

| EP | 0344992 A1 | 2/1989 | |
| WO | WO -8606577 A1 * | 11/1986 | ............... A01G 9/00 |
| WO | 02/094416 A1 | 11/2002 | |
| WO | 2014/024211 A2 | 2/2014 | |
| WO | 2016/074032 A1 | 5/2016 | |

* cited by examiner

METHOD AND APPARATUS FOR REGENERATION, ACCLIMATIZATION, AND CONDITIONING OF PLANT PROPAGULES

BACKGROUND OF THE INVENTION

Field of the Invention

Embodiments of the invention relate to cultivation of higher plants and, more specifically, to a method and apparatus for the regeneration, acclimation and conditioning of in vitro derived plant propagules.

This invention has particular, but not exclusive, applications to a plant propagation and cultivation method for regenerating, acclimating and conditioning medicinal plantlets derived from in vitro micropropagated propagules (callous, nodal segments, somatic embryo, rootless shoots, rooted shoots). For illustrative purposes citations will be further described with reference to this application. However, it is to be understood that this method and apparatus could be used in other applications such as regenerating, acclimatizing and conditioning micropropagated propagules generally.

Description of the Related Art

Plant tissue culture refers to various methods which have been developed for the propagation of plants, in which isolated segments of the plants, referred to as explants, are surface sterilized, inoculated onto a sterile growth media, incubated according to specific temperature and irradiance levels, and grown in vitro. Generally speaking, the stages consist of establishing an explant to in vitro conditions, multiplication of the donor material to produce many potential explants, induction of shoots, elongation of shoots, induction of root formation on shoots, and finally acclimatization of the shoots to an ex-vitro environment. The type or form of the in vitro growth is controlled by varying the composition of the growth media. This includes varying the concentration of carbohydrate, agar, nutrients, and most significantly the types and concentration of Plant Growth Regulators (PGRs).

Typically, such methods involve subculturing explants on solidified growth media, and require technical expertise, specialized equipment, and skilled labour in subculturing between each of the individual stages of the micropropagation protocol. This involves significant expense with respect to the skilled labour, and inputs costs such as a solidifying agent added to the media composition. As such, plant tissue culture practitioners have developed methods and apparatuses that utilize liquid media in bioreactors, eliminating the costly solidifying agent, allowing for media renewal in process, reducing the labour associated with subculturing. Although beneficial developments for the field, such methods and apparatus have not rectified the consequences of in vitro growth on plant physiology, susceptibility to harmful microflora or the reliance on skilled technician labour and other laboratory equipment (autoclave, laminar flow work bench etc.) and require a distinct acclimatization phase. Solutions are often propagules specific, (i.e. for rootless shoots only, method and apparatus not compatible with somatic embryos or other in vitro derived propagules) limiting the scope of their application. Furthermore, such apparatuses require autoclaving before use and set up under aseptic laboratory conditions.

A consistent problem throughout the field of micropropagation is the physiological changes associated with in vitro growth. More specifically the high humidity, reliance on organic carbohydrates as an energy source, low irradiance, and low concentration of $CO_2$ in the in vitro environment, result in plant materials which cannot adequately regulate their osmotic pressure or produce sufficient energy through photosynthesis. This leads to unviable plantlets which succumb to desiccation in the lower ambient humidity of the ex vitro environment, or starvation from lack of energy when cut off from supply of organic carbohydrate. As such, methods which have successfully demonstrated in vitro plantlet multiplication and regeneration fail to become commercially viable due to low survivability of plantlets in the ex vitro environment. Practitioners have developed rudimentary methods and/or apparatus which allow incremental exposure of in vitro derived shoots or plantlets to ex vitro conditions. The plantlets are exposed to the ex-vitro environment in discrete stages such that over all survivability is increased. Methods and apparatus include vented lids of tissue culture vessels, acclimatizing in high humidity nurseries, acclimatizing in vented domes, acclimatization in humidity controlled greenhouses and other variations which allow partial control of humidity and irradiance leading to stomata and photosynthetic conditioning allowing plants to avoid desiccation and starvation in the ex vitro environment. Some apparatuses have combined rooting and acclimatization of plantlets into one phase, but have not incorporated shoot organogenesis, or plantlet acclimation to biotic factors (microbiota).

A further difficulty with micropropagation is the vulnerability of micropropagated and acclimatized plantlets is their susceptibility to microflora and pathogens with adverse impacts on plants physiology and productivity. This is of particular concern in the cultivation of medicinal plants as bacteria and fungi could render the dried herbal product unfit for human consumption, particularly those microbiota that produce dangerous secondary metabolites. In vivo grown plants must be viewed as living systems whose tissues are occupied by bacteria and fungi, and often such relationships are fundamental to the survival and productivity of plants (i.e. mycorrhizal fungi, nitrogen fixing bacteria). By virtue of the aseptic nature of micropropagation such relationships cannot exist, making them particularly vulnerable to colonization by pathogenic microbiota. Such problems are generally overcome through the application of pesticides and fungicides, or irradiation of the finished herbal product. However, the use of petrochemicals on agricultural products is a growing concern for consumers, and often their use is associated with a perceived reduction in finished product quality. Reactive methods to control microflora in finished products, such as gamma-irradiation (cold-pasteurization) also present consumer concern, and are limited in that they cannot remove pathogenic metabolites even if the underlying microbiota is neutralized.

The use of controlled growth environments for the cultivation of plants generally and, more specifically for the cultivation of medicinal plants, is becoming increasingly important. Due to advances in indoor agricultural practices and energy efficiency improvements in artificial lighting, higher quality products can be manufactured in high-intensity cultivation systems. Such systems utilize levels of irradiance and $CO_2$ much higher than ambient conditions leading to increased system efficiency. In order to harness the full productive capacity of such systems plants may require conditioning to high intensity conditions, which generally would be accomplished as a separate vegetative growth phase following the acclimatization or conversion of plantlets.

The commercial use of tissue culture propagules (micropropagation) in control environments horticulture is relatively limited as a consequence of the specialized equipment and expertise necessary to achieve an aseptic conditions and conduct skilled tasks proscribed by the existing tissue culture protocols. Although advances have been made, there is significant room for improvement in both methods and apparatuses to further consolidate the stages of regeneration, reduce the expertise required, acclimate plantlets to biotic factors, and condition them metabolically and morphologically for high intensity cultivation in an indoor growth environ.

BRIEF SUMMARY OF THE INVENTION

The present invention provides a method and apparatus for the regeneration, acclimatization, and conditioning of plant propagules for ex vitro production conditions. One or more embodiments of the present invention comprises a propagule chamber characterized by autonomous or semi-autonomous regulation of its environ wherein plant propagules can be placed. The apparatus further comprises a laminar flow work station fold out and a supply chamber.

One or more embodiments of the invention comprise a process control system. The process control system controls both biotic and abiotic factors that impact propagule development. It regulates the atmospheric composition of the environ, the level and quality of irradiance, as well as the frequency, duration, and composition of media which irrigates the propagules. The device can be 'cleaned in place' and achieve aseptic conditions within the environ prior to its use. The environ can be loaded with aseptic propagules and nutritional media without the introduction of biological contamination. The process control system is able to suppress and disinfect potential biological contamination to the environ during its operation. These capabilities allow the device to conduct various processes associated with in vitro tissue culture protocols including germination, conversion, shoot induction, shoot elongation, root initiation, root elongation, and/or root proliferation, within a single device, and without the need for frequent subculturing for each in vitro process.

Furthermore, the regulation of conditions within the environ allows for the acclimatization of plantlets to ex vitro biotic and abiotic conditions. This is achieved through the gradual increase in irradiance and carbon dioxide levels, the gradual decrease in humidity, as well as the introduction of a benign or beneficial microbiota to uncolonized plant tissues. The combined effect is to ensure lower mortality and higher plant vigour of propagules transitioning from in vitro to ex vitro conditions in this device than could be accomplished otherwise.

Furthermore, the regulation of abiotic factors within the environ allows for the metabolic and morphological conditioning of plantlets for desirable characteristics. These characteristics may include those which would result in greater productivity of the plantlet throughout its life cycle. Examples would include the selective irradiance or plantlets with wavelengths of light that promote greater leaf surface area, shorter plant stature, shorter internode length, increased chloroplast density, or increased stomata density. This conditioning for production specific purposes consists of aspects beyond the scope of acclimatization, and is better characterized as plant conditioning.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION

The present invention comprising a method and apparatus for the regeneration, acclimatization, and conditioning of plant propagules for ex vitro production will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an exemplary order to provide an understanding of one or more systems and methods, the exemplary order is not meant to be limiting. One of ordinary skill in the art would recognize that the steps or processes may be performed in a different order, and that one or more steps or processes may be performed simultaneously or in multiple process flows without departing from the spirit or the scope of the invention. In other instances, specific features, quantities, or measurements well known to those of ordinary skill in the art have not been described in detail so as not to obscure the invention. It should be noted that although examples of the invention are set forth herein, the claims, and the full scope of any equivalents, are what define the metes and bounds of the invention.

For a better understanding of the disclosed embodiment, its operating advantages, and the specified object attained by its uses, reference should be made to the accompanying drawings and descriptive matter in which there are illustrated exemplary disclosed embodiments. The disclosed embodiments are not intended to be limited to the specific forms set forth herein. It is understood that various omissions and substitutions of equivalents are contemplated as circumstances may suggest or render expedient, but these are intended to cover the application or implementation.

The term "first", "second" and the like, herein do not denote any order, quantity or importance, but rather are used to distinguish one element from another, and the terms "a" and "an" herein do not denote a limitation of quantity, but rather denote the presence of at least one of the referenced item.

One or more embodiments of the present invention will now be described with references to FIGS. 1-15

Figure 14:
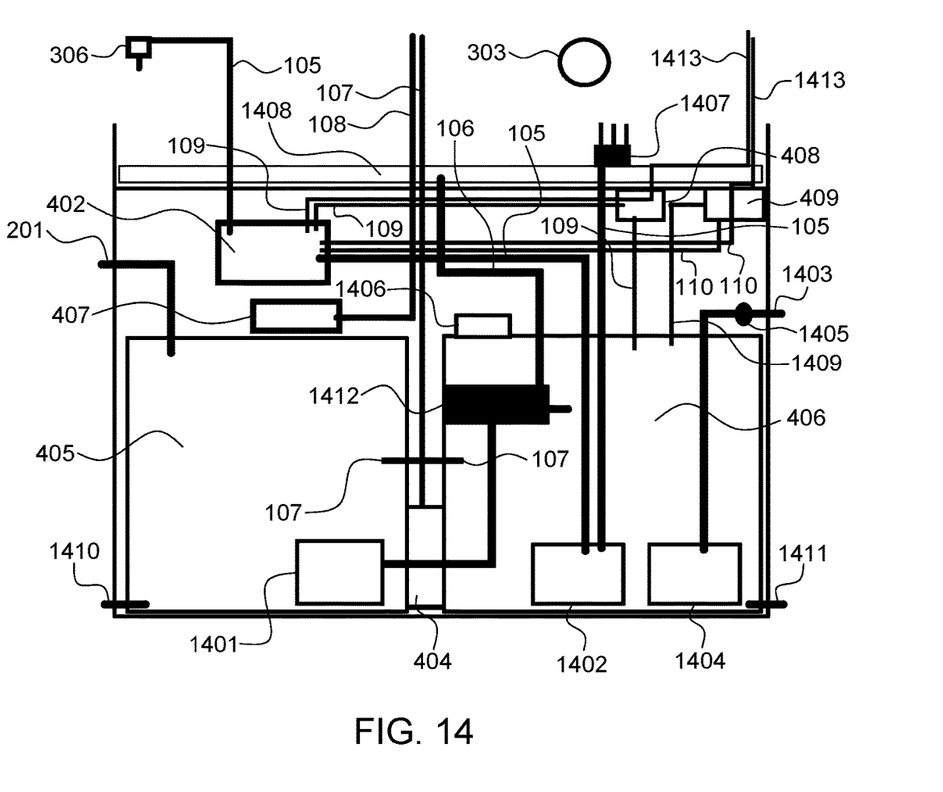
FIG. 14 is a schematic illustration of the nutritional delivery system in accordance with one or more embodiments of the present invention.
Figure 15:
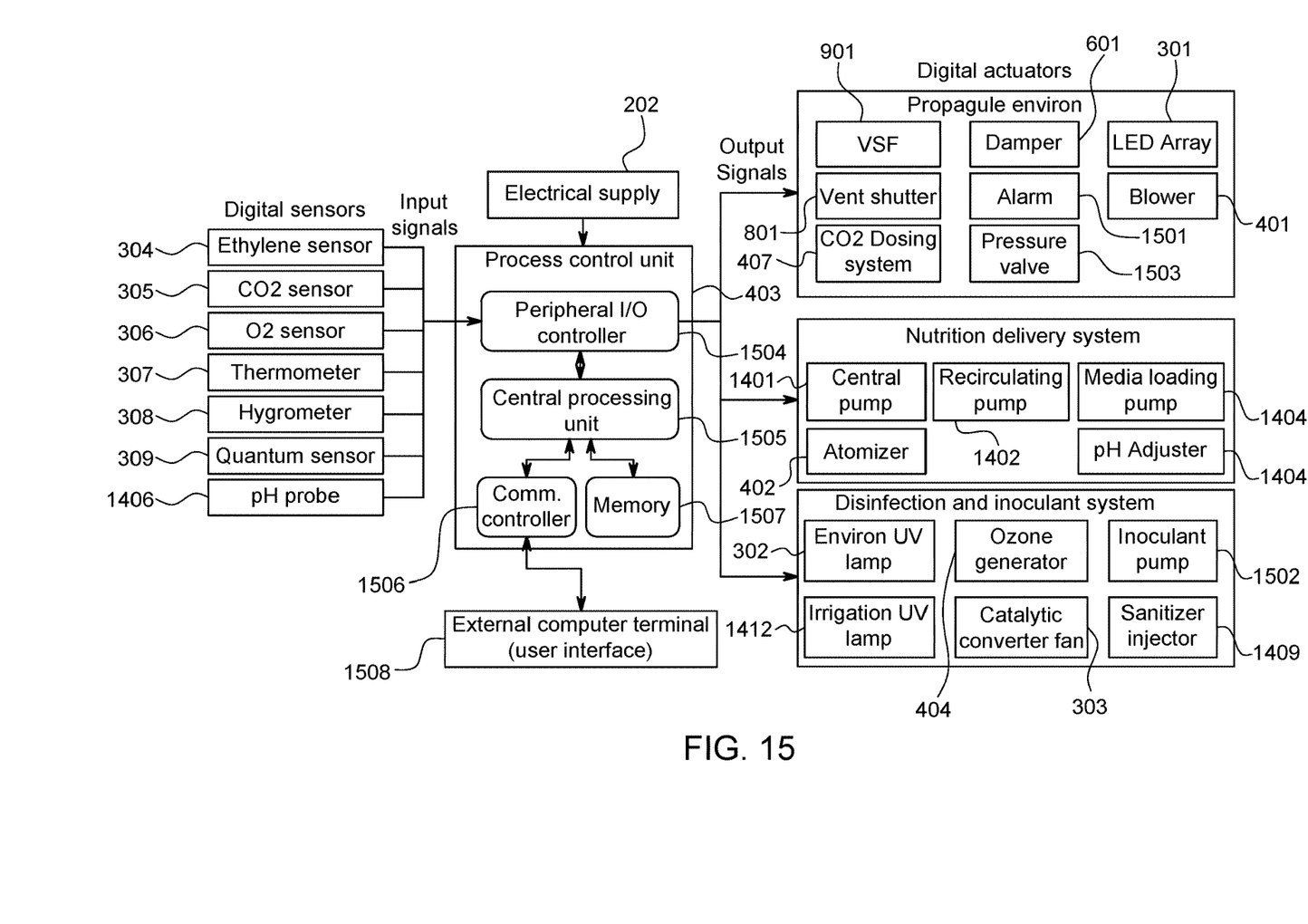
FIG. 15 is an illustration of the process control system in accordance with one or more embodiments of the present invention.

The Propagule Finishing Apparatus (hereafter the PFA) (100) is an apparatus that maintains the appropriate biotic and abiotic conditions for the regeneration, acclimatization, and conditioning of in vitro derived plant propagules and plant propagules generally. The PFA (100) comprises an Integrated Laminar-flow Workstation (FIGS. 10-13) coupled to a Propagule Environ (101) and an Equipment Housing Compartment (102). The Equipment Housing Compartment (102) comprises a Nutrition Delivery System (FIG. 14), an Inoculant System (FIG. 14) and a Disinfection System (FIG. 14). Each of these components are monitored and modulated by a Process Control System (FIG. 15).

Figure 1:
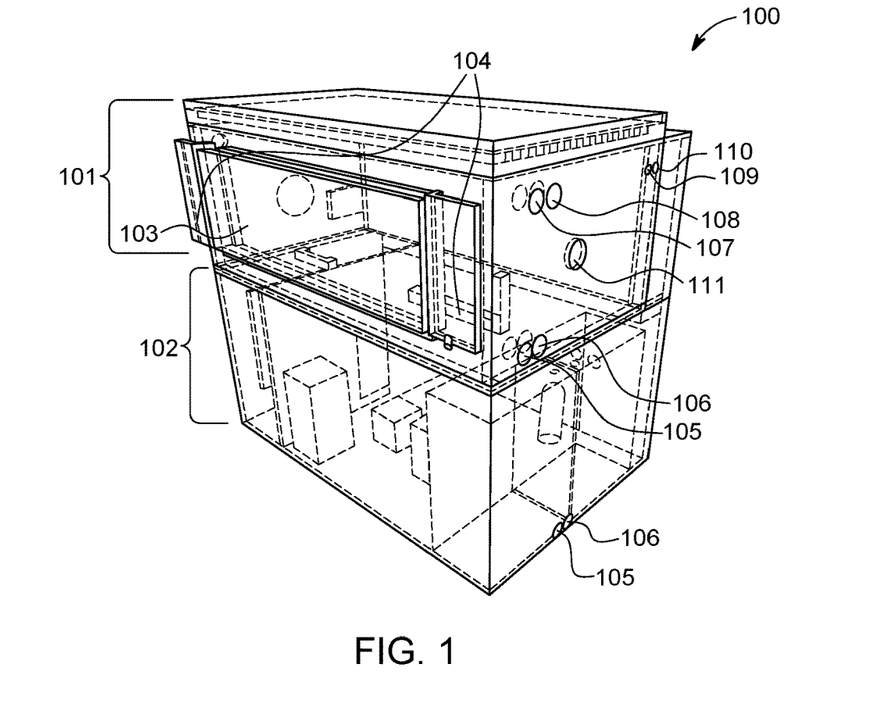
FIG. 1 is an illustration of a front isometric view a propagule finishing apparatus in accordance with one or more embodiments of the present invention.
Figure 2:
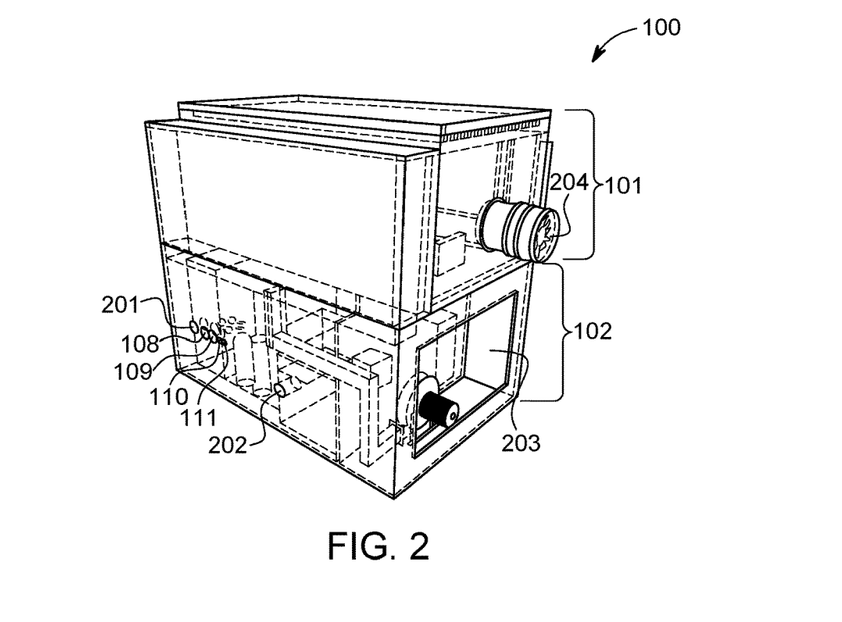
FIG. 2 is an illustration of a rear isometric view of the propagule finishing apparatus in accordance with one or more embodiments of the present invention.
Figure 3:
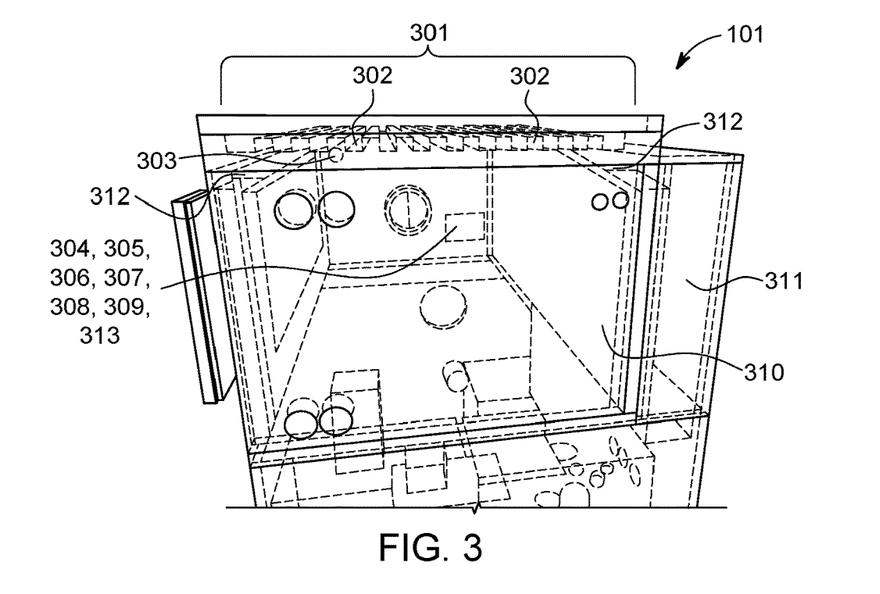
FIG. 3 is an illustration of a side perspective view of the propagule environ in accordance with one or more embodiments of the present invention.
Figure 4:
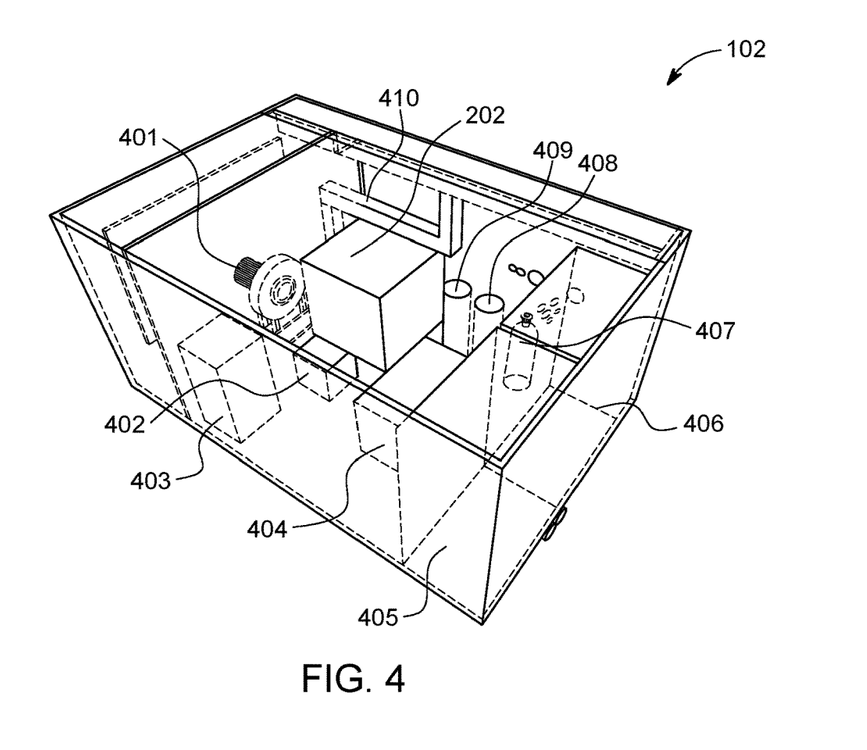
FIG. 4 is an illustration of a front isometric view of the equipment housing compartment in accordance with one or more embodiments of the present invention.
Figure 5:
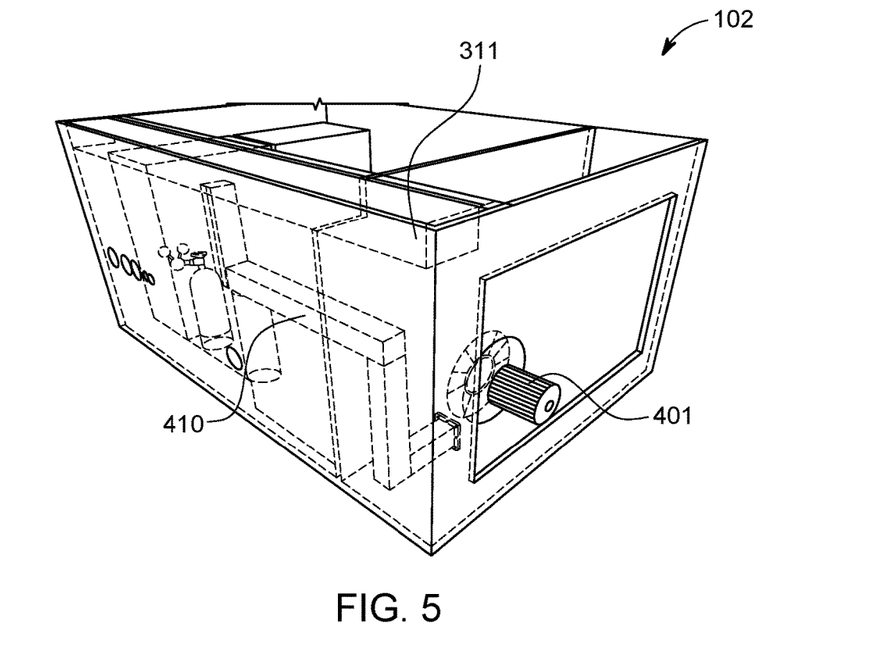
FIG. 5 is an illustration of a rear isometric view of the equipment housing compartment in accordance with one or more embodiments of the present invention.
Figure 6:
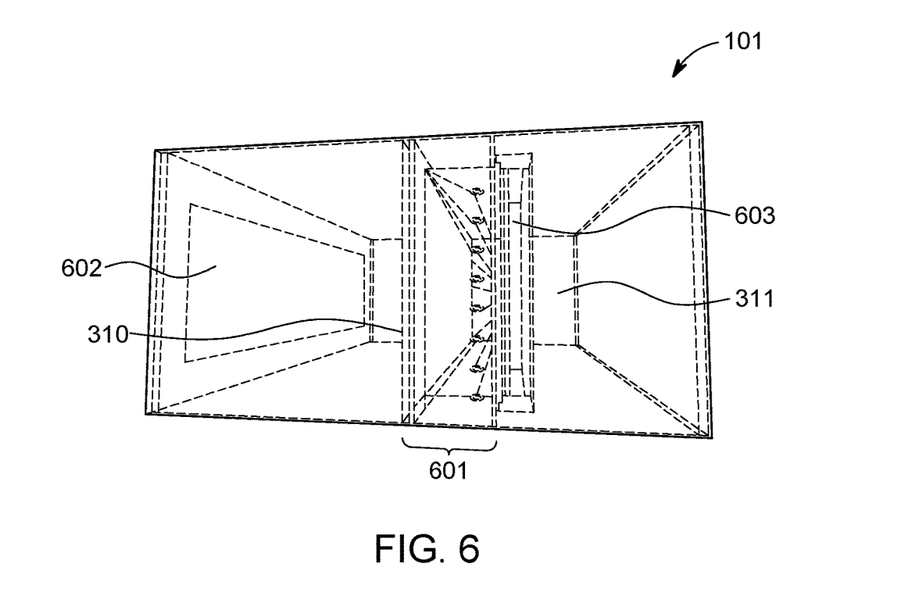
FIG. 6 is an illustration of a right side isometric view of the propagule environ with the damper in a closed position.
Figure 7:
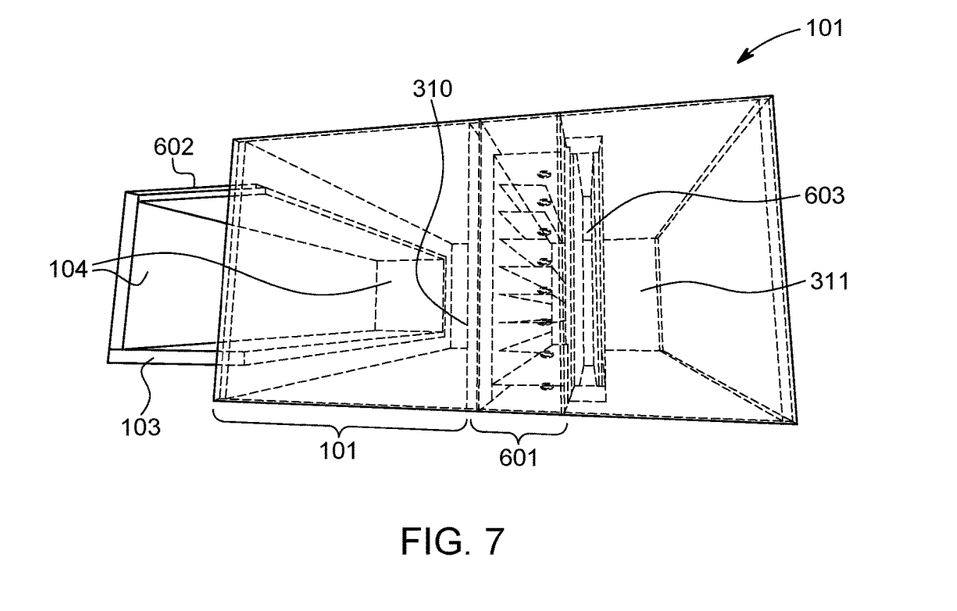
FIG. 7 is an illustration of a right side isometric view of the propagule environ with the workstation in a deployed position.

In one or more embodiments, the Propagule Environ is a chamber of a cuboid shape with a transparent observation port and/or Access Door (602) to allow observation of the propagules throughout the finishing process. The Propagule Environ (101) may be illuminated from above by an array of light emitting sources. For instance, these illumination sources may include narrow-band emissions from Light Emitting Diodes (LEDs) (301) of wavelengths in the 450-470 nm, 525-545 nm, 650-670 nm, and 720-740 nm ranges. The Propagule Environ (101) may be made of any suitable material, e.g., stainless steel.

Figure 8:
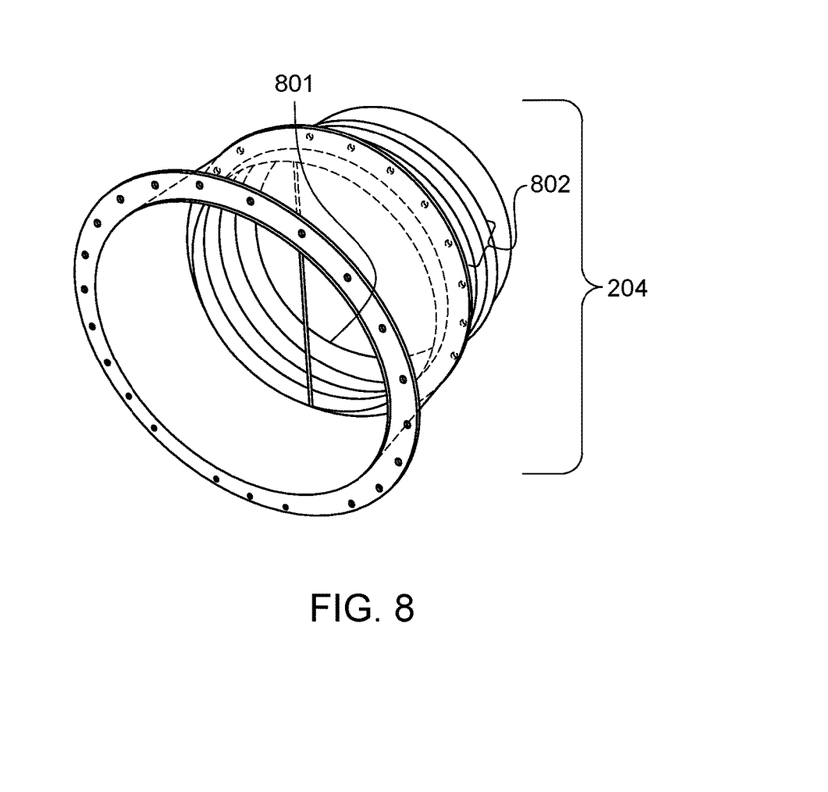
FIG. 8 is an illustration of the intake vent port in a closed position.
Figure 9:
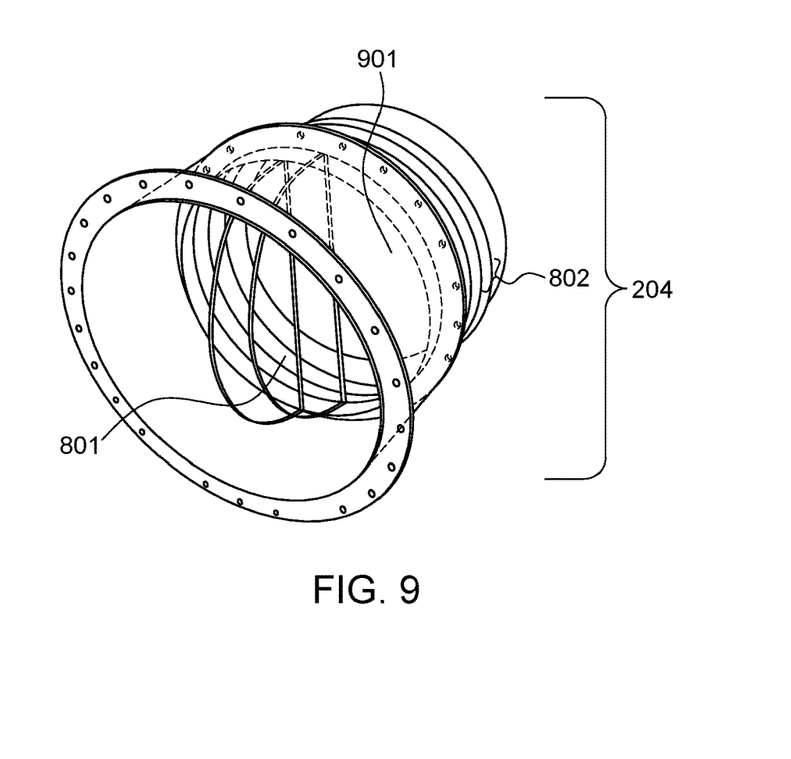
FIG. 9 is an illustration of the intake vent port in an open position.
Figure 10:
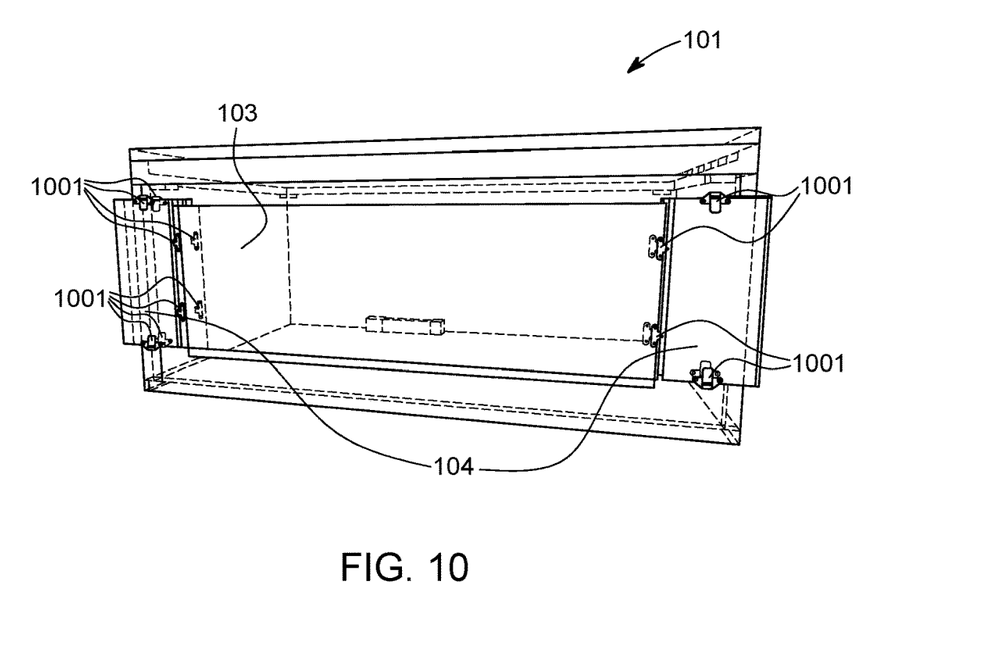
FIG. 10 is an illustration of a front perspective view of the propagule environ with the workstation fold outs in a closed position.
Figure 11:
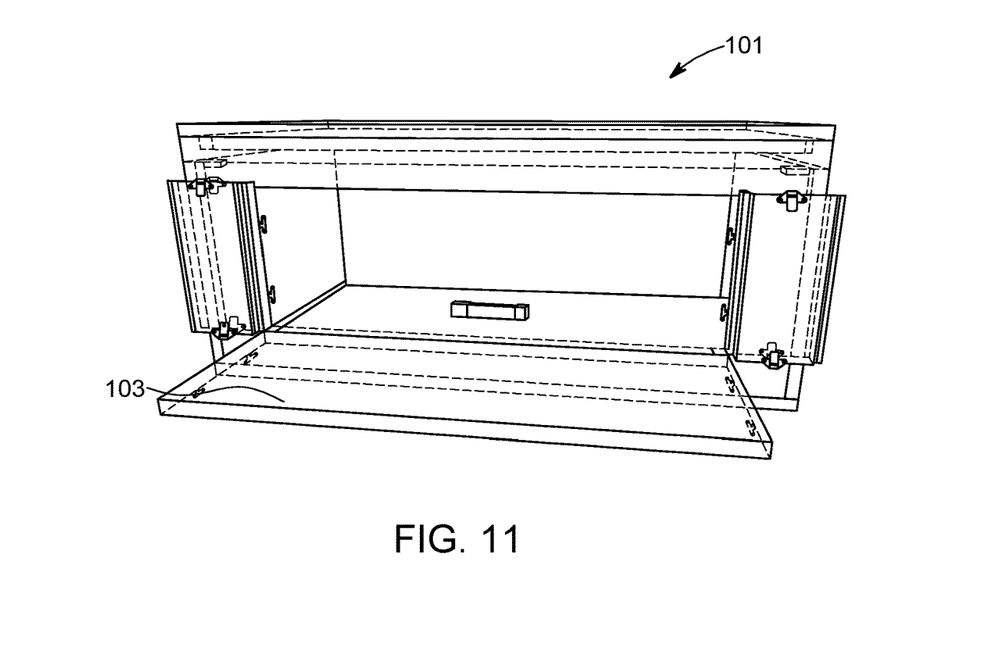
FIG. 11 is an illustration of a front perspective view of the propagule environ with the bottom workstation fold out in a deployed position.
Figure 12:
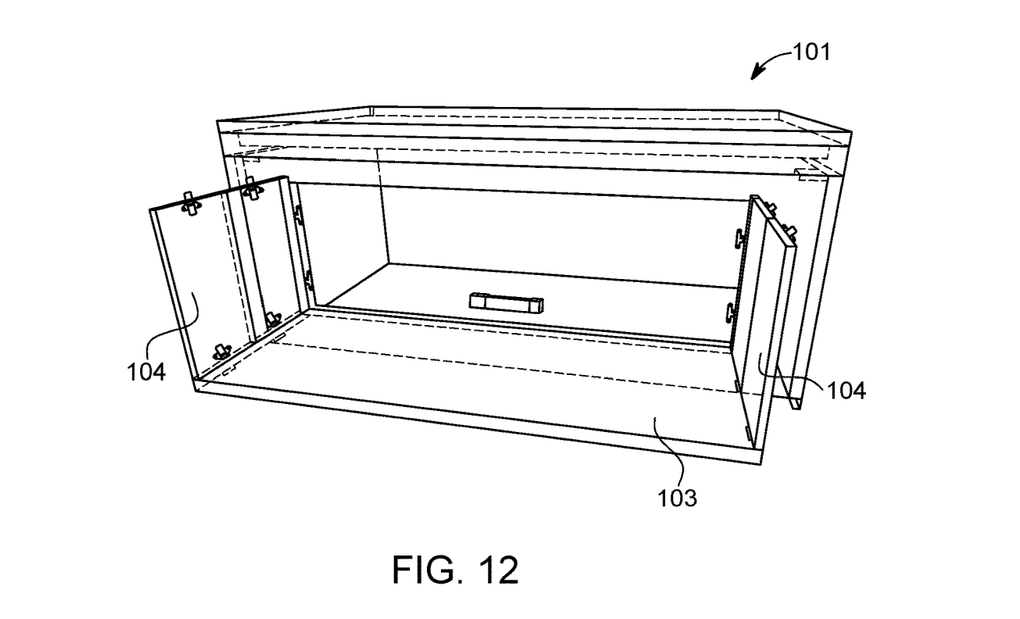
FIG. 12 is an illustration of a front perspective view of the propagule environ with the bottom and side workstation fold outs in a deployed position.
Figure 13:
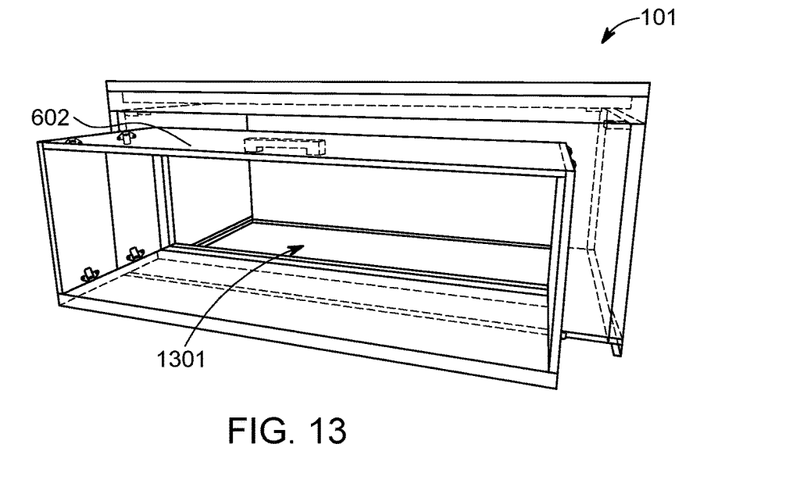
FIG. 13 is an illustration of a front perspective view of the propagule environ with the full workstation fold outs in a deployed position.

The Propagule Environ (101) may further comprise one or more vent ports, e.g. Intake Vent Port (204) and Exhaust Vent Port (111). The Intake Vent Port (204), comprises a Variable Speed Fan (VSF) (901), a Vent Shutter (801), and an In-line HEPA Filter (802). The Exhaust Vent Port (111) comprises a one-way Pressure Valve (1503). The Pressure Valve (1503) can be locked in the closed position. When the Vent Shutter (801), Pressure Valve (1503), Access Door (602), and Damper (601) are closed, the Propagule Environ (101) becomes hermetically sealed. The Propagule Environ (101) further comprises a Carbon Dioxide Dosing System (407) (also "CO2 Regulator"), such as a canister of CO2, which can regulate the concentration of carbon dioxide inside the atmosphere of the Propagule Environ (101) by delivering CO2 from the CO2 Regulator (407) to the Propagule Environ (101) through the Carbon Dioxide Supply Line (108).

In one or more embodiments, the Integrated Laminar-Flow Workstation, which is contiguous with the Propagule Environ (101), comprises a Pre-Filter (203), HEPA Filter (603), Blower (401), Blower Ducting (410), Plenum (311), Damper (601), Laminar Diffuser (310), Access Port (1301), Access Door (602), a Base Workstation Fold Out (103) and two Side Workstation Fold Outs (104). The three Workstation Fold Outs (WFOs) are located on the exterior of the Propagule Environ (101), surrounding the Access Door (602). In the retracted position, the WFOs rest flat against the external side of the front face of the propagule environ (101) and surrounding the Access Door (602). When in the extended position, the WFOs fold out and are secured with Clasps (1001) perpendicular to the front face of the Propagule Environ (101), and in conjunction with the Access Door (602) in the open position, surrounding the periphery of the Access Port (1301) on all four sides and create an airtight seal between the WFOs and the Propagule Environ (101) as well as between the abutting WFOs and Access Door (602). The lower of the Workstation Fold Out (103) is attached to the propagule environ at the base of the Access Door (602), and is secured on the outside of the access door (602) when in the closed position, while the side Workstation Fold Outs (104) are attached on the left and right of the access door (602) and rest on the outside of the Propagule Environ (101) when in the closed position.

The Integrated Laminar-Flow Workstation may be deployed by lowering the base WFO (103), and moving the side WFOs (104) such that they are perpendicular to the front side of the Propagule Environ (101). The base WFO (103) fits into and is supported by the side WFOs (104), which can be clasped together to form air tight seals around the Access Port (1301) of the Propagule Environ (101) and between the WFOs. Once the WFOs have been deployed, the Blower (401) is turned on, the Damper (601) is opened and the Access Door (602) is opened upwards to become a top WFO and clasped to the side WFOs. These elements combine to provide laminar flow across the Propagule Environ (101) that travels though the Access Port (1301) and across the WFOs. The airflow created by the Integrated Laminar-Flow Workstation delivers an approximate velocity of 0.5 m/s through the WFOs, creating a suitable laminar flow workspace for loading or accessing the Propagule Environ (101) while maintaining sterility.

One or more embodiments of the present invention further comprises a Nutrition Delivery System for irrigating the Propagule Environ with water, plant growth regulators, carbohydrate and chemical nutrition. The Nutrition Delivery System is a fertigation system that operates in closed-loop, recirculating fashion. It comprises a Water Intake (201), a Main Reservoir (405), a Main Reservoir Drain Port (1410), a Recirculating Reservoir (406), a Recirculating Reservoir Drain Port (1411), a Central Pump (1401), a Recirculating Pump (1402), a Media Loading Port (1403), a Media Loading Pump (1404), a Media Loading Filter (1405), a pH Adjustor (1406), a propagule environ Media Supply Line (105), a Distributor (1407), an Atomizer (402), a Misting Supply Line (1413), a Misting Nozzle (312), a Collector (1408), a Media Return Line (106), a Sanitizer Tank (409), a Sanitizer Supply Line (110), and a Sanitizer Injector (1409). The Water Intake (201) is connected to the Main Reservoir (405) which may be filled from an external source. The Main Reservoir (405) is connected to the Recirculating Reservoir (406) which is filled by the Main Reservoir (405), by the Central Pump (1401). The Main Reservoir (405) and the Recirculating Reservoir (406) each possess a drain port which can empty the contents of these tanks. The Recirculating Reservoir (406) is connected to the Media Loading Port (1403) and is filled with media through the Media Loading Filter (1405). Loading media into the Recirculating Reservoir (406) involves the Media Loading Pump (1404) directing sterile water from the Main Reservoir (405) into pre-filled bags of sterile media. The mixed media then passes through the Media Loading Filter (1405) into the Recirculating Reservoir (406).

The pH Adjustor comprises a pH Probe (1406) to measure pH in the Recirculating Reservoir (406), one or more pH Tanks holding acidic, basic, and/or buffer solutions, and an injector which provide signal input to, are controlled by the Process Control System, to deliver the solutions from the pH Tanks into the Recirculating Reservoir (406). The Recirculating Pump (1402) delivers media from the Recirculating Reservoir (406), through the Supply Line (105) and the Distributor (1407), to irrigate the Propagule Environ (101) and the plant tissues it contains. The media, having irrigated the propagules in the Propagule Environ (101), drains to the Collector (1408), and is directed through the Return Line (106), back to the Recirculating Reservoir (406). Alternatively, the Recirculating Pump (1402) can deliver media, from the Recirculating Reservoir (406), through the Atomizer Supply Line (105) to the Atomizer (402), which aerosolizes the media and directs it into the atmosphere of the Propagule Environ (101) through the Misting Nozzle (312).

One or more embodiments of the present invention further comprises a Disinfection System. The Disinfection System comprises a number of components including a germicidal Environ UV Lamp (302) which can illuminate the Propagule Environ. The Disinfection System further comprises a germicidal Irrigation UV Lamp (1412) in the Recirculating Reservoir (406), which irradiates the recirculating media solution. The Disinfection System also comprises an Ozone Generator (404) which can diffuse the oxidizing gas through the Ozone Supply Lines (107), into the solutions in the Recirculating Reservoir (406) and Main Reservoir (405), and also into the Propagule Environ (101). Contained within the Propagule Environ (101) is a Catalytic Converter (303), which when activated, recirculates the gases using a Catalytic Converter Fan (not shown) and catalyzes the degradation of the ozone back into oxygen. Furthermore, the Environ UV Lamp (302) can be activated to enhance the degradation of ozone in the Propagule Environ (101).

The Disinfection System further comprises the Atomizer (402) and Sanitizer Tank (409) which is capable of fumigating the Propagule Environ (101) with chemical sterilizing agents. The Supply Line (109) is also connected to the Sanitizer Injector (1409) which can direct chemical sanitizing agents, such as peroxides, from the Sanitizer Tank (409), through the Supply Line (109), the Distributor (1407), the Propagule Environ (101), the Collector (1408), the Return Line (106), and the Recirculating Reservoir (406).

One or more embodiments of the present invention further comprises an Inoculant System, consisting of an Inoculant Tank (408), an Inoculant Pump (1502), Inoculant Supply Lines (109), and the Atomizer (402) which can fumigate inoculant into the Propagule Environ (101). The Inoculant Pump (1502), which may be located in the Inoculant Tank (408), directs beneficial microbiota carried in solution, to either the Atomizer (402), or the Recirculating Reservoir (406) through the Inoculant Supply Line (109). The Atomizer (402) is capable of fumigating the Propagule Environ (101) with the desired microbiota, to facilitate the colonization of leaf and stem tissues, while the inoculant directed to the Recirculating Reservoir (406) can be irrigated through the Nutrition Delivery System to facilitate the colonization of propagule root tissues. This initial exposure to microbiota from aseptic in vitro conditions provides propagules with a benign or beneficial microflora, enhancing their resistance to potential pathogens the propagules may be exposed to after leaving the PFA, or enhancing plant metabolic function through mechanisms such as increased nutrient uptake.

One or more embodiments of the present invention further comprises a Process Control System (PCS). The PCS comprises a number of digital sensors, to receive and relay signals to a Peripheral I/O Controller (1504); one or more Process Control Units (403) (PCU), which uses a Central Processing Unit (1505) to compute control commands using the information from the sensors and algorithms stored on the PCU's Memory (1507); and based on the result of this computation outputs signals from the PCUs to various actuators, e.g. digital actuators, and other components detailed herein. Examples of actuators in the Propagule Environ are VSF (901), Damper (601), LED Array (301), Vent Shutter (801), Alarm (1501), Blower (401), CO2 Dosing System (407), Pressure Valve (1503). Examples of actuators in the Nutrition Delivery System are Central Pump (1401), Recirculating Pump (1402), Media Loading Pump (1404), Atomizer (402), and pH Adjuster (1406). Examples of actuators in the Disinfection System and Inoculant System are Environ UV Lamp (302), Ozone Generator (404), Inoculant Pump (1502), Irrigation UV Lamp (1412), Catalytic Converter Fan (303) and Sanitizer Injector (1409).

The Process Control System primarily regulates four functions.

Regulation of the microenvironment—The PCS regulates the microenvironment of the Propagule Environ (101). In one or more embodiments, the Propagule Environ (101) is equipped with a number of digital sensors, such as a Carbon Dioxide Sensor (305), an Oxygen Sensor (306), an Ozone Sensor (313), a gas-phase Ethylene Sensor (304), a digital Thermometer (307), a digital Hygrometer (308), and a sensor for the quantification of illuminance, such as a Quantum Sensor (or illuminometer) (309). The PCS integrates the information derived from these sensors with the algorithms programmed on the PCU Memory, and outputs signals which modulate the state of the Intake Shutter (801), the Intake Variable Speed Fan (901), etc. The combination of these components provides the ability to control the exchange of gases between the inside of the Propagule Environ (101) and the external environment, thereby allowing for the venting of undesirable atmospheric conditions such as excess heat, excess ethylene, and excess humidity. The Nutrition Delivery System and the CO2 Dosing System (407) provide sources of desired inputs to the microenvironment in order to adjust for low ambient humidity and/or CO2 levels of the gases introduced to the Propagule Environ (101) through the Intake Vent Port (204). Furthermore, the aggregate level of irradiance, and the spectral distribution of light emitted from the LEDs (301), can be modulated by the PCS, either by varying the input voltages to the LEDs (301), adjusting the frequency of current provided to the LEDs (301), or the selective activation and deactivation of individual LEDs of different wavelengths.

Regulation of the Nutrition Delivery System—The PCS can regulate the periodicity and duration of the fertigation cycle based on the input from the Hygrometer (308), as well as the set-points and algorithms stored in the Memory (1507). In one or more embodiments, the Recirculating Pump (1402) is of a variable speed which can adjust the flowrate or misting frequency of the media which irrigates the Propagule Environ (101).

Regulation of the Disinfection System—The PCS can regulate the Clean-in-Place program such that ozonation, Germicidal UV, peroxides and other sterilants are dosed in a sufficient manner to create sterile conditions inside the Propagule Environ (101) and Nutrient Delivery System.

Regulations of the Inoculant System—The PCS can regulate the delivery of inoculant to the Propagule Environ (101) through the Nutrient Delivery System and Atomizer (402), by activating the Inoculant Pump (1502) to mist and/or irrigate the Propagule Environ (101) with microbiota as described in the Inoculation subheading below.

Clean-in-Place:

In one or more embodiments, the Propagule Environ (101) can be cleaned in place, prior to loading with propagules, using the Disinfection System to create aseptic or near sterile conditions inside the chamber. Additionally, the Access Door (602) allows the operator to access each of the surfaces inside the chamber, which can be cleaned of any debris, and surface sterilized. Components that could be used for the regeneration, acclimatization and conditioning of propagules (substrate, tray etc.) can also be sterilized using the Clean-in-Place disinfection program. The components are cleaned of any debris by the operator, and placed inside Propagule Environ which has also been surface sterilized by the operator. The Propagule Environ (101) is then hermetically sealed by closing the Access Door (602) and locking the Pressure Valve (1503) in the closed position. The 'Clean-in-Place' disinfection program is selected by the operator using the User Interface (1508), transmitted to the PCU through the Communication Interface (1506), and the PCS closes the Damper and Vent Shutter, then activates the Sanitizer Injector (1409) and Recirculating Pump (1402) to push chemical disinfectants from the Sanitizer Tank (409) through the components of the Nutrition Delivery System. Simultaneously, the PCS activates the Atomizer (402) which draws chemical sanitizer from the Sanitizer Tank (409) and fumigates the Propagule Environ (101). Subsequently, the chemical sanitizer collects in the Recirculating Reservoir (406) and is drained from the apparatus. In the next phase of the Clean-in-place disinfection program, the Ozone Generator (404) is activated by the PCS to dose the Propagule Environ (101) with ozone. In one or more embodiments, concentrations of ozone present inside the Propagule Environ (101) remain above 5 part per million of a period of time exceeding 2 hours. Afterwards, the Catalytic Converter Fan within the Catalytic Converter (303) is activated by the PCS to recirculate the ozone enriched atmosphere of the Propagule Environ (101) across the catalysing surfaces inside the Catalytic Converter (303) which degrades residual ozone. Simultaneous to the operation of the Catalytic Converter (303), the Environ UV emitter (302) is activated by the PCS and further catalyses the degradation of ozone. The use of UV at this stage serves a dual purpose of also irradiating the surfaces of the Propagule Environ (101) to provide additional disinfection. In one or more embodiments, the aggregate dose of UV irradiance on the surfaces of the Propagule Environ (101) is at least 25,000 micro joules per square centimeter. Upon completion of the Clean-in-Place cycle, the Recirculating Reservoir (406) is refilled with water from the Main Reservoir (405), and the Intake Shutter (801) and Pressure valve (1503) are opened, and the Variable-Speed Fan (901) of the Intake Vent creates a positive pressure within the Propagule Environ (101) which vents the remaining gases through the Pressure Valve (1503). The system is now considered aseptic and ready to be loaded with propagules. The order and inclusion of each of the phases of the Clean-in-Place sterilization cycle, described above, should not be considered the sole method contemplated by the present invention. Those of skill in the arts would appreciate that other combinations, permutations, and sequences are within the scope of the invention.

Loading:

In one or more embodiments, the Integrated Laminar-Flow Workstation is deployed, following the Clean-in-Place sterilization cycle, to allow for the aseptic loading of propagules into the Propagule Environ (101). The Integrated Laminar-Flow Workstation is deployed as described above. Within the workstation, the operator can transfer sterile propagules into the Propagule Environ (101) through the Access Port (1301) without introducing biological contamination. As an additional procedure, aspects of the Clean-in-Place disinfection cycle can be run again as a precaution against biological contamination present on the propagules themselves or contamination introduced by the operator as a function of poor aseptic technique while loading. The intensity of the disinfection interventions in the methods described above, would be scaled down so as not to damage the propagules.

Clean-in-Process:

The Clean-in-Process function of the PCS is directed toward the suppression and disinfection of biological contamination that may be introduced to the PFA (100) during its operations. It is a function that is engaged as part of the programming associated with the operation of the Nutrition Delivery System and controlled by the PCS. It comprises two forms of disinfection, the use of germicidal UV inside the Recirculating Reservoir (406), as well as ozonation of water held within the Main Reservoir (405) and Recirculating Reservoir (406), if media components are stable. These forms of disinfection operate either continuously or intermittently during the operation of the Nutritional Delivery System, and serve to keep any exogenous microbiota below impactful levels.

Regeneration:

In one or more embodiments, propagules for regeneration include sterile rootless shoots, auxiliary buds, nodal segments, encapsulated nodal segments, somatic embryos, encapsulated somatic embryos, desiccated somatic embryos, callous, embryogenic callous, and/or seeds.

After disinfecting and loading the Propagule Environ (101) as described above, the Damper (601) is closed and the Propagule Environ (101) is hermetically sealed as to maintain near 100% relative humidity. The appropriate nutritional cycle for the type of regeneration desired may be selected by an operator, through a User Interface (not shown), and transmitted to the PCS through the communication interface (1506), e.g. Ethernet Connection. The PCS controls the Nutrient Delivery System to cause the propagules in the Propagule Environ (101) to be irrigated (immersed or misted) with media formulated for desired growth characteristics from the Recirculating Reservoir (406). The irrigation cycle (duration and frequency of immersion/misting) is controlled by the PCS, and can be set according to a propagule specific schedule.

As an example, without limiting the generalization of methods that can be employed in the apparatus, an encapsulated nodal segment, commonly referred to as a synthetic seed, could be irrigated with a shoot elongation media for 2 minutes 5 times daily for 2 weeks, then with a root initiation media for 30 seconds 2 times daily for 2 weeks to complete the conversion of the synthetic seed into a plantlet. It should be understood that any in vitro derived propagule could be used as a starting material and the regeneration protocol adapted to the specific needs of that propagule. The provided example is but one rendition of a method made possible by this apparatus.

In one or more embodiments, the Disinfection System can also suppress biological contamination in the Propagule Environ (101) and Nutrition Delivery System during the regeneration, acclimatization, and conditioning of plant propagules. Unlike other regenerative equipment, the PFA (101) can reduce the microbiological load throughout the processes, mitigating production risks, and loss associated with contamination.

The Nutrition Delivery System uses the Recirculating Pump (1402) to direct the desired media onto the propagules in the Propagule Environ (101). The media is drained back to the Recirculating Reservoir (406) by virtue of gravity. The Recirculating Reservoir (406) is equipped with a germicidal UV emitter which disinfects the media 'in-process'. In one or more embodiments, the Irrigation UV Lamp (1412) irradiates the solutions contained within the Recirculating Reservoir (406) which supplies media to the Propagule Environ (101).

In one or more embodiments, the Nutrition Delivery System works in conjunction with the environmental controls of the Propagule Environ (101) and adjusts them to achieve specific conditions. The irrigation fluid supplied by the Nutrition Delivery System contributes to the relative humidity in the Propagule Environ (101). The level of humidity can be regulated by the PCS. Upregulation is achieved by misting sterile water from the Main Reservoir (405), through the Atomizer (402) and Misting Nozzle (312) to increase humidity in the Propagule Environ (101). Downregulations is achieved by exchanging gases from the external environment with that which is in the Propagule Environ (101), through the Intake Vent (204) and Exhaust Vent (111). The PCS regulates these systems to achieve the appropriate level of humidity (100%-45% relative humidity) for the particular stage of propagule development.

Once the propagules have developed their photosynthetic capacity, the atmosphere in the Propagule Environ (101) can be supplemented with CO2 from the Carbon Dioxide Regulator (407) and the quality and quantity of irradiance can be adjusted. Together these factors drive higher photosynthetic and growth rates of the propagules. The media can be exchanged 'in-process' to direct the type of growth exhibited by the propagules. The ability to modulate these factors within a single environ eliminates any handling of propagules between stages of development, reducing costs and simplifying the micropropagation protocols. The immersion time and frequency, photoperiod, intensity of irradiance (20 $\mu mol\ m^{-1}s^{-1}$-900 $\mu mol\ m^{-1}s^{-1}$) and concentration of CO2 (250 $\mu mol\ mol^{-1}$-750 $\mu mol\ mol^{-1}$) can be adjusted and automated by the PCS in accordance with the programmed algorithms. The Ethylene Sensor (304) which samples the atmosphere within the Propagule Environ (101) can detect (1-200 $\mu mol\ mol^{-1}$) the presence of ethylene, an indicator of decaying plant material. Upon a predetermined threshold, programmed into the PCS memory, an Alarm (1501) (e.g. visual, audio, digital) is triggered and notification may be sent to the operator through an IP connection. Such plant materials can be extracted 'in-process' to avoid any potential impact of ethylene gas on the other developing plantlets. This is accomplished by deploying the Integrated Laminar-Flow Workstation as described, aseptically removing the problem material and resealing the Propagule Environ (101). The regeneration protocol can proceed as scheduled. The data collected by the aforementioned sensors is stored on the PCS memory and transmitted to the operator for review. Other such sensor reading which exceed the deviations preprogrammed in the PCS memory, similarly trigger an alarm with audio, visual, and/or digital notifications to the operator.

Acclimatization:

Abiotic Acclimatization—In one or more embodiments, following the regeneration and conversion of the propagules into plantlets (having both an established shoot and root system) the PCS modulates the abiotic and biotic factors acting on the propagules to acclimate the plantlets from the in vitro environmental conditions to the ex vitro environmental conditions. The gradual changes of abiotic factors in the Propagule Environ (101), including relative humidity (lowering from ~100% to 45% RH), atmospheric composition (increase CO2 concentration), quantity of irradiance, composition of chemical nutrition, and the duration and periodicity of irrigation. The PCS gradually reduces the humidity in the Propagule Environ (101) according to a preprogrammed schedule, such that the plantlets acquire the capability of homeostatic osmoregulation without stress associated with a large fluctuation. Concurrently, the carbohydrate source is removed from the media source in a graduated fashion, while the irradiance and CO2 concentration in the atmosphere are gradually increased to drive photosynthesis.

Biotic Acclimatization—Once the carbohydrate has been completely removed from the media, which provided a necessary energy source before plantlets were photoautotrophic, the propagules can be inoculated with benign microbiota. The inoculant can be delivered to the plantlets carried by irrigation from the Nutrition Delivery System, thereby exposing inoculant to the roots, or as a fumigant provided by the Atomizer (402) into the Propagule Environ (101), exposing inoculant to plant tissues. This benign microbiota readily colonizes the plant tissues providing bio protection through spatial occupation, precluding the establishment of undesired microbiota which the plantlets may be exposed to outside of the Propagule Environ (101). The selective inoculation of microbiota represents the biotic aspect of the acclimatization of plantlets to the ex vitro environment.

The synergistic control of these variables allows precise control over the initiation of photoautotrophic and osmoregulation improving the survivability of micropropagated plantlets in the ex vitro environment. Throughout the acclimatization process the Disinfection System suppresses any undesired microbiota in the Nutrition Delivery System. Unlike existing systems, the regeneration and acclimatization occurs in conjunction without handling of the plantlets, and acclimates them both the abiotic (low relative humidity, high irradiance, no carbohydrate source) and biotic (microbiota) factors.

Inoculation:

In one or more embodiments, the inoculant provided to the plantlets, can consist of a benign microbiota, as part of the acclimatization process, or a beneficial symbiont which improves the plantlets metabolic capacity and is better described as part of plantlet conditioning process. The benefits of symbiotic microbiota are well known in the art and serve multiple purposes including increased uptake of organic nutrients, increase plant productivity, increased biomass accumulation, and enhancement of a plant's natural immune response to pathogens, among others. The selection of the inoculant type would be a function of the conditioning desired for the intended cultivation conditions.

In one or more embodiments, when the propagules are of medicinal plants to be used as herbal medicines, the desirable benign inoculants are those microbiotas which show no sporulation in the intended cultivation conditions, do not negatively affect the physiology of the plantlet or mature plant in any capacity, do not produce dangerous secondary metabolites, and when subjected to a drying process, are neutralized. The beneficial symbiont microbiotas have the aforementioned characteristics alongside a positive impact on plant physiology, productivity, or disease resistance. Some isolates of *Clonostachys rosea* are examples of microbiota which meet this specification. By controlling the plant microbiome in such a manner, regulatory requirements to achieve certain microbial thresholds for herbal medicines can be met without the use of irradiation, reducing the cost of manufacturing and enhancing consumer perception of quality. This prophylactic use of inoculant also precludes the contamination of herbal products with pathogenic metabolites, toxins which cannot be remediated by irradiation.

Conditioning:

Subsequent to the regeneration and acclimatization of plantlets, the PFA (100) can condition plantlets (also referred to as 'plant training') inside the Propagule Environ (101), such that they are morphologically and metabolically preconditioned for their intended cultivation conditions and/or purpose.

In one or more embodiments, the PCS regulates the biotic and abiotic factors within the Propagule Environ (101) in accordance with the preprogrammed conditioning algorithms held in the memory of the PCS.

In one or more embodiments, the aspects of the PFA (100) which provide utility in the conditioning of plantlets include the Nutrition Delivery System, the Inoculant System, and the control of abiotic factors in the Propagule Environ (101). Factors which can be modulated to induce desired plantlet metabolic and morphological responses may include the aggregate level of irradiance, the spectral composition of irradiance, the atmospheric levels of carbon dioxide, and the inoculation with beneficial microbiota.

Within the Propagule Environ (101), the range in intensity of irradiance can achieve overall photosynthetic photon flux density between 20 $\mu mol\ m^{-1}s^{-1}$ to 900 $\mu mol\ m^{-1}s^{-1}$ as required for the conditioning program. The composition of irradiance can also be adjusted by varying the ratio of red spectrum (630 nm peak emission) and blue spectrum (460 peak emission) emission. This ratio can be varied between 1:9 to 1:1. Furthermore, the range in concentration of Carbon dioxide inside the Propagule Environ (101) can range between 400 $\mu mol\ mol^{-1}$-1300 $\mu mol\ mol^{-1}$ as required by the conditioning program.

The PCS can regulate the quantity and quality of the irradiance, in conjunction with the concentration of CO2 in the Propagule Environ's atmosphere, to direct the growth of the plantlets for a desired morphology (i.e. short internode length, increased leaf surface area, increase stem diameter, suppression of apical dominance). The conditioning program may use all of or any combination of the components of the conditioning system.

In one or more embodiments, morphological conditioning of floral medicinal plants involves the use of changes in both the quality and quantity of irradiance. These factors can be used to decrease internode length, increase shoot proliferation, and increase stem rigidity. Denser internode spacing results in more compact floral products, often preferred in the context of medical floral products. Shoot tips are considered to be the most productive floral area of the plant, hence increasing the number of shoots from a plant increases its floral capacity by increasing the ratio of floral to non-floral biomass accumulation. Furthermore, medicinal flowering plants can exhibit a concentration gradient of active ingredient from top to bottom. By directing the plant growth to multiple short stature shoots, the chemical gradient can be minimized improving product homogeneity and consistency.

In one or more embodiments, the PCS can adjust the peak irradiance to a blue spectrum (460 nm) for the purposes of morphological conditioning involving the reduction of internode length, inhibition apical dominance to encourage shoot proliferation, and an increase stem diameter.

In one or more embodiments, the PCS can adjust the peak irradiance, quantity of irradiance, concentration of CO2, fertigation profile and atmospheric humidity in order to increase chlorophyll capacity, condition endogenous photoprotection mechanisms, and increase stomatal conductance for the purpose of metabolic conditioning. Such conditioning will prepare the plantlets for high intensity cultivation conditions such as indoor artificial lighting applications. The PCS can regulate the peak irradiance to the blue peak to increase stomatal aperture while dosing CO2 to the Propagule Environ (101) working synergistically to increase stomatal conductance, encouraging the assimilation of CO2 through photosynthesis. Once in a high stomatal conductive state, the PCS can switch between high irradiance (>300 $\mu mol\ m^{-1}s^{-1}$) in the red spectrum to drive photosynthesis and low irradiance with a blue peak to increase stomatal aperture, and quickly switch between such conditions driving photosynthesis. The PCS can regulate the Nutrition delivery system in conjunction with the irradiance such that sufficient humidity, and nutrition is available for the plants to harness the increase photosynthetic potential and biomass accumulation made possible by the metabolic conditioning. The irradiance can be gradually increased such that the plantlets are physiologically capable of harnessing the increase productive capacity made possible from high irradiance and CO2 concentration associated with high intensity indoor cultivation.

In one or more embodiments, the plantlet develops its photoprotection mechanisms, increases its stomatal density, increases its chlorophyll content in response to the metabolic conditioning such that its can delay photoinhibition and be optimally productive in high CO2 and irradiance cultivation.

This apparatus simplifies to process of tissue culture plant regeneration and eliminates the requirement of trained lab technicians and laboratory equipment. The PFAs makes it possible for someone unskilled in the art to fully regenerate screen and selected elite cultivars across the plant kingdom, be they angiosperm (monocots or dicots) or gymnosperms. This versatility is possible by the ability to program the PFAs parameters to an established micropropagation protocol.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for plantlet regeneration, acclimatization, and conditioning, comprising:
    a propagule chamber in which plant tissues are aseptically regenerated under controlled environmental conditions;
    an Integrated Laminar-Flow Workstation for accessing and aseptic loading of propagules in the propagule chamber;
    an equipment housing comprising components for nutrition delivery, inoculant delivery and disinfection; and
    a Process Control System for regulating the operations of the propagule chamber's environmental controls, the components for nutrition delivery, inoculant delivery and disinfection.

2. The apparatus in claim 1, wherein the propagule chamber is a cuboid shaped structure with an access port on a front side of the structure and an access door hingedly coupled to the top of the access port for sealing the access port.

3. The apparatus in claim 2, wherein the Integrated Laminar-Flow Workstation comprises a base workstation foldout hingedly coupled to the bottom of the access port, and two side workstation foldouts each hingedly coupled to one side of the access port.

4. The apparatus in claim 3, wherein the Integrated Laminar-Flow Workstation further comprises a plenum chamber coupled to a backside of the propagule chamber with a diffuser configured as a wall separating the plenum chamber from the propagule chamber.

5. The apparatus in claim 4, wherein the Integrated Laminar-Flow Workstation further comprises a filter and a damper between the plenum chamber and the propagule chamber.

6. The apparatus in claim 1, wherein the Process Control System comprises one or more sensors coupled to the propagule chamber for obtaining information about the environmental conditions in the propagule chamber and using the information as feedback to control one or more vent ports in the propagule chamber.

7. An apparatus for plantlet regeneration, acclimatization, and conditioning, comprising:
a propagule chamber in which plant tissues are aseptically regenerated, acclimatized, and conditioned under controlled environmental parameters, wherein a front side of the propagule chamber comprises an Access Port and an Access Door for the Access Port;
an integrated workstation for accessing and aseptic loading of propagules in the propagule chamber, wherein the integrated workstation comprises a Base Workstation Fold Out and two Side Workstation Fold Outs coupled on the front side of the propagule chamber; and
an equipment housing comprising components for nutrition delivery, inoculant delivery and disinfection.

8. The apparatus in claim 7, further comprising a Process Control System for regulating operations of the propagule chamber's environmental controls, the components for nutrition delivery, the inoculant delivery and the disinfection.

9. The apparatus in claim 8, wherein the integrated workstation further comprises a plenum chamber coupled to a diffuser at a backside of the propagule chamber.

10. The apparatus in claim 7, wherein the propagule chamber is a cuboid shaped structure with an access port on a front side of the structure and an access door hingedly coupled to the top of the access port for sealing the access port.

11. The apparatus in claim 10, wherein the Integrated Laminar-Flow Workstation comprises a base workstation foldout hingedly coupled to the bottom of the access port, and two side workstation foldouts each hingedly coupled to one side of the access port.

12. The apparatus in claim 11, wherein the Integrated Laminar-Flow Workstation further comprises a plenum chamber coupled to a backside of the propagule chamber with a diffuser configured as a wall separating the plenum chamber from the propagule chamber.

13. The apparatus in claim 12, wherein the Integrated Laminar-Flow Workstation further comprises a filter and a damper between the plenum chamber and the propagule chamber.

14. An apparatus for plantlet regeneration, acclimatization, and conditioning, comprising:
a propagule chamber in which plant tissues are aseptically regenerated under controlled environmental conditions;
an Integrated Laminar-Flow Workstation for accessing and aseptic loading of propagules in the propagule chamber;
a Nutrition Delivery System for aseptically irrigating the plant tissues within the propagule chamber with various types of nutritional media;
an Inoculant System for controlling delivery of inoculant to the propagule chamber;
a Disinfection System for controlling microbiota in the Nutrition Delivery System and sterilizing the propagule chamber; and
a Process Control System for regulating the operations of the propagule chamber's environmental conditions, Nutrition Delivery System, the Inoculant System and the Disinfection System.

15. The apparatus in claim 14, wherein the Process Control System comprises one or more sensors coupled to the propagule chamber for obtaining information about the environmental conditions in the propagule chamber and using the information as feedback to control one or more vent ports in the propagule chamber.

16. The apparatus in claim 15, wherein the one or more sensors is selected from a group comprising a Carbon Dioxide Sensor, an Oxygen Sensor, an Ozone Sensor, a gas-phase Ethylene Sensor, a digital Thermometer, a digital Hygrometer, and a sensor for the quantification of illuminance such as an illuminometer.

17. The apparatus in claim 15, wherein the one or more vent ports comprises an intake vent port and an exhaust vent port.

18. The apparatus in claim 14, wherein the propagule chamber is a cuboid shaped structure with an access port on a front side of the structure and an access door hingedly coupled to the top of the access port for sealing the access port.

19. The apparatus in claim 18, wherein the Integrated Laminar-Flow Workstation comprises a base workstation foldout hingedly coupled to the bottom of the access port, and two side workstation foldouts each hingedly coupled to one side of the access port.

20. The apparatus in claim 19, wherein the Integrated Laminar-Flow Workstation further comprises a plenum chamber coupled to a backside of the propagule chamber with a diffuser configured as a wall separating the plenum chamber from the propagule chamber.

21. The apparatus in claim 20, wherein the Integrated Laminar-Flow Workstation further comprises a filter and a damper between the plenum chamber and the propagule chamber.

* * * * *